United States Patent
Alitalo et al.

(10) Patent No.: US 9,527,759 B2
(45) Date of Patent: Dec. 27, 2016

(54) METHOD FOR TREATING AND/OR PRETREATING LIQUID MANURE OR BIOGAS PLANT REJECT FOR THE ELIMINATION OF HARMFUL SUBSTANCES, PARTICULARLY NITROGEN, PHOSPHORUS, AND ODOR MOLECULES

(75) Inventors: Anni Alitalo, Jokioinen (FI); Erkki Aura, Tammela (FI); Risto Seppälä, Matku (FI)

(73) Assignee: Pellon Group Oy, Yilhärmä (FI)

( * ) Notice: Subject to any disclaimer, the term of this patent is extended or adjusted under 35 U.S.C. 154(b) by 1314 days.

(21) Appl. No.: 12/937,604

(22) PCT Filed: Apr. 24, 2009

(86) PCT No.: PCT/FI2009/050328
§ 371 (c)(1),
(2), (4) Date: Dec. 13, 2010

(87) PCT Pub. No.: WO2009/130396
PCT Pub. Date: Oct. 29, 2009

(65) Prior Publication Data
US 2011/0113840 A1    May 19, 2011

(30) Foreign Application Priority Data
Apr. 25, 2008    (FI) .................................. 20085371

(51) Int. Cl.
C05F 3/00    (2006.01)
C12M 1/00    (2006.01)
(Continued)

(52) U.S. Cl.
CPC ................. C02F 3/121 (2013.01); A01C 3/00 (2013.01); C02F 1/20 (2013.01); C05F 17/0018 (2013.01);
(Continued)

(58) Field of Classification Search
CPC .......... A01C 3/00; C12M 21/04; C12M 29/18; C12M 23/58; C12M 47/18; C02F 3/121; C02F 2303/02; C02F 2101/16; C02F 2103/20; C02F 1/5245; C02F 1/66; C02F 11/04; C02F 2101/105; C02F 2203/004; C02F 2301/08; C05F 3/00; C05F 17/0027; Y02W 30/47; Y02W 30/43; Y02W 10/15; Y02P 20/145; Y02E 50/343
(Continued)

(56) References Cited

U.S. PATENT DOCUMENTS 3,929,600 A * 12/1975 Hiasa et al. .................. 210/668
5,811,287 A     9/1998 Aoshima
(Continued)

FOREIGN PATENT DOCUMENTS

JP        9262600        10/1997
JP    2004-008843 A      1/2004
(Continued)

OTHER PUBLICATIONS

KIPO Machine Translation of KR 2002-0030764, accessed online Mar. 21, 2014, pp. 1-17.*
(Continued)

Primary Examiner — William H Beisner
Assistant Examiner — Danielle Henkel
(74) Attorney, Agent, or Firm — Womble Carlyle Sandridge & Rice LLP

(57) ABSTRACT

The invention relates to a method and an apparatus for treating and/or pre-treating liquid manure or biogas plant reject for eliminating harmful substances, particularly nitrogen, phosphorus, and odor molecules. Process tanks (5), which include inlet means (4) for supplying a process tank (5) with a substance to be treated, outlet means for passing a post-treatment matter out of the tank, and air inlet means (Continued)

(2) for supplying the process tank with air required by a biological process, are used for conducting a biological treatment on the matter to be treated. The process tanks (5) are first provided with a microbe population adapted for treating the matter to be treated. The matter to be treated is supplied gradually into the first process tank and then further into a subsequent process tank, such that the microbe population initially provided in the process tanks displaces in a step-by-step manner the original microbe population present in the matter to be treated. The matter, which is substantially free of the original microbes and has been expelled from the final process tank, is returned into the first process tank for diluting the matter to be treated. Downstream of the process tanks is conducted a nitrogen removal treatment by feeding the matter to be treated from the process tank (5) of a stripping tower (22A), in which the pH of a matter to be treated has been raised by means of a biological treatment to a level sufficient from the standpoint of nitrogen removal.

9 Claims, 1 Drawing Sheet

(51) Int. Cl.

| | | |
|---|---|---|
| C02F 3/12 | (2006.01) | |
| C02F 1/20 | (2006.01) | |
| A01C 3/00 | (2006.01) | |
| C05F 17/00 | (2006.01) | |
| C12M 1/107 | (2006.01) | |
| C02F 1/66 | (2006.01) | |
| C02F 101/16 | (2006.01) | |
| C02F 103/20 | (2006.01) | |
| C02F 1/52 | (2006.01) | |
| C02F 11/04 | (2006.01) | |
| C02F 101/10 | (2006.01) | |

(52) U.S. Cl.
CPC ....... *C05F 17/0027* (2013.01); *C05F 17/0045* (2013.01); *C12M 21/04* (2013.01); *C12M 23/58* (2013.01); *C12M 29/18* (2013.01); *C12M 47/18* (2013.01); *C02F 1/5245* (2013.01); *C02F 1/66* (2013.01); *C02F 11/04* (2013.01); *C02F 2101/105* (2013.01); *C02F 2101/16* (2013.01); *C02F 2103/20* (2013.01); *C02F 2203/004* (2013.01); *C02F 2301/08* (2013.01); *C02F 2303/02* (2013.01); *Y02E 50/343* (2013.01); *Y02P 20/145* (2015.11); *Y02W 10/15* (2015.05); *Y02W 30/43* (2015.05); *Y02W 30/47* (2015.05)

(58) Field of Classification Search
USPC .................................. 71/6; 435/283.1, 294.1
See application file for complete search history.

(56) References Cited

U.S. PATENT DOCUMENTS

| 6,866,779 | B1 * | 3/2005 | Burke | 210/603 |
|---|---|---|---|---|
| 2002/0079266 | A1 * | 6/2002 | Ainsworth | C02F 3/28 210/603 |
| 2006/0141605 | A1 * | 6/2006 | Kumar | C12R 1/01 435/262.5 |
| 2008/0302722 | A1 * | 12/2008 | Burke | 210/603 |

FOREIGN PATENT DOCUMENTS

| KR | 20020030764 | 4/2002 |
|---|---|---|
| KR | 20020031916 | 5/2002 |
| NL | 8801827 A | 10/1989 |
| RU | 2067967 | 10/1996 |

OTHER PUBLICATIONS

Seminar Presentation, Kokkonen et al., MTT Agrifood Research Finland; published on Feb. 19, 2008; https://portal.mtt.fi/portal/Artturi/Artturikirjasto/Artturikoulutus/Lantaseminaari_2008/Erkki_Aura.pdf.

Cultivation Service Statistics, Manure Statistics, 2002-2004; http://www.viljavuuspalvelu.fi/viljavuuspalvelu/user_files/files/kotielain/lanta_tilastot.pdf.

Rappert et al., "Microbial Degradation of Selected Odorous Substances," *Waste Management*, 2005, pp. 940-954, vol. 25.

* cited by examiner

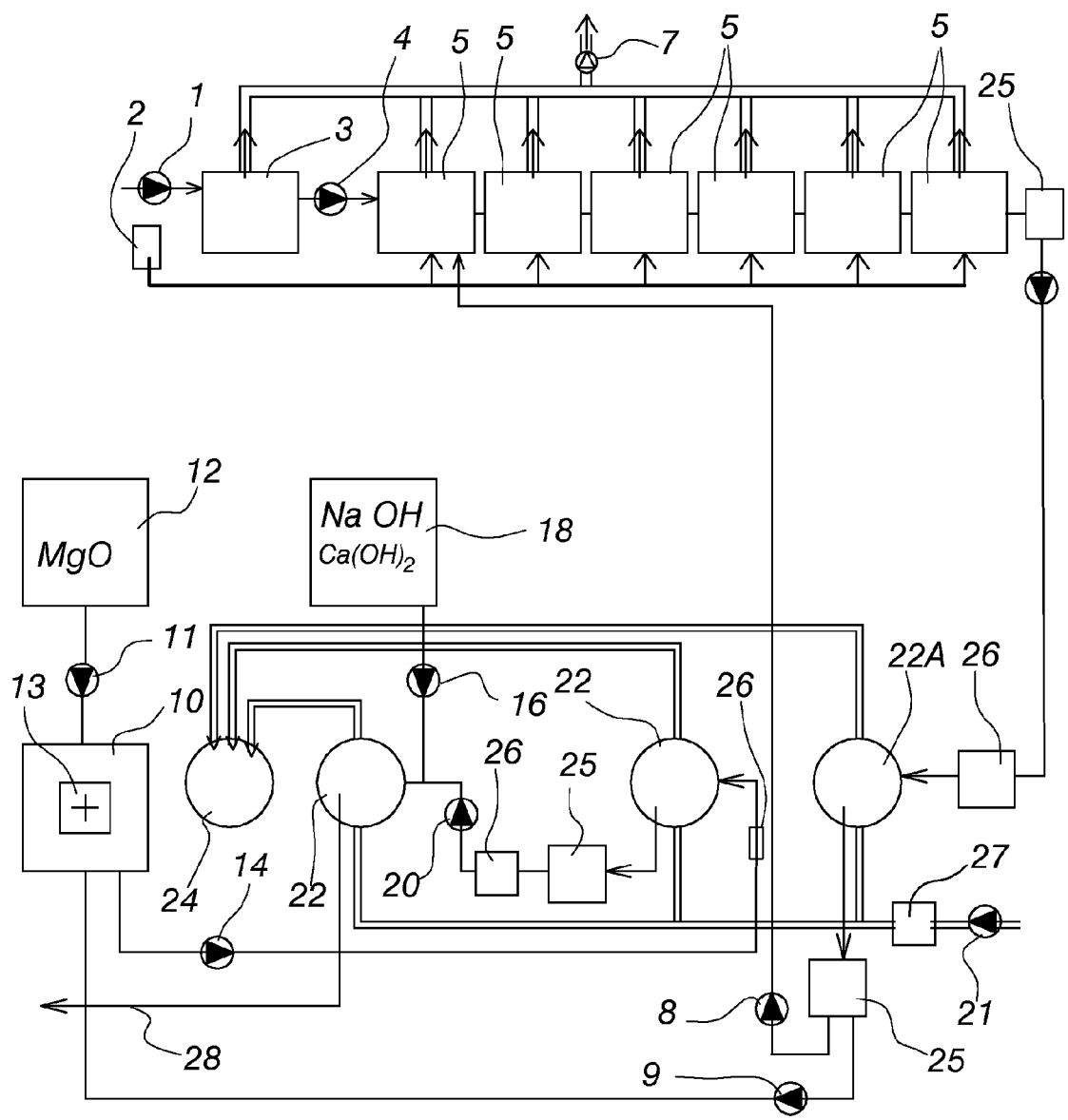

METHOD FOR TREATING AND/OR PRETREATING LIQUID MANURE OR BIOGAS PLANT REJECT FOR THE ELIMINATION OF HARMFUL SUBSTANCES, PARTICULARLY NITROGEN, PHOSPHORUS, AND ODOR MOLECULES

CROSS-REFERENCE TO RELATED APPLICATIONS

This application is a national stage filing under 35 U.S.C. 371 of PCT/FI2009/050328 filed Apr. 24, 2009, which International Application was published by the International Bureau in English on Oct. 29, 2009, which claims priority to Finnish Patent Application No. 20085371, filed on Apr. 25, 2008, which are both hereby incorporated herein in their entirety by reference.

BACKGROUND

Field of the Disclosure

The present invention relates to a method for treating and/or pre-treating liquid manure or biogas plant reject for the elimination of harmful substances, particularly nitrogen, phosphorus, and odor molecules.

Description of Related Art

As a consequence of the general intensification of agriculture, the increased farm sizes, the concentration of farming in specific regions and, on the other hand, the specialization of farms in a given line of production, have resulted in a situation where more nutrients are produced than can be spread out on the fields. The situation has culminated in centralized biogas facilities, in which the digestion process is supplied with nutrient-rich feed materials from outside the farm. Nutrients originating from agriculture have been found to constitute the main source of eutrophication in waterways. The runoff of nitrogen is the most important environmental hazard caused by nitrogen losses. The nitrate resulting from nitrification has a particular propensity to runoff. The nitrogen load of a water system causes the overgrowth of nitrogen-limited algae and thereby deteriorates the quality of water. The runoff of nitrogen into potable water reserves may cause health risks in case the nitrogen content is excessively high.

In a particular effort to reduce nutrient runoffs to natural waters, the nitrogen fertilization has been limited by legislation. The nitrates directive issued by the European Union restricts the amount of nitrogen allowed for spreading on the fields. Therefore, some of the farms are forced to remove nutrients further away or completely outside the farm's boundaries. However, most of the liquid manure volume consists of water. This leads to substantial transport and spreading costs. Along with the quantitative production, there are also other problems relevant to using the nitrogen of liquid manure as a fertilizer. The fertilization value of liquid manure nitrogen is difficult to estimate as some of the liquid manure nitrogen is in an organic state. Organic nitrogen is not in the form directly useful for plants, but it is only gradually released into an inorganic form that plants are able to use. On the other hand, some of the liquid manure nitrogen may be lost as gaseous nitrogen emissions, either during storage, at the moment of spreading or immediately after spreading as ammonia gas emissions or by denitrification as nitrogen oxides and/or a nitrogen gas. Hence, the fertilization value of liquid manure nitrogen fluctuates more than that of mineral fertilizers. Because the nitrogen fertilization effect is difficult to estimate, this easily leads to the fertilization being over- or undervalued. In light of the foregoing reasons, there is a demand for methods useful for I) concentrating or separating nitrogen from liquid fraction
II) converting liquid manure nitrogen into a form that enables utilizing the fertilization value of liquid manure nitrogen as effectively as possible and thereby reduces the need of using mineral fertilizers.

With regard to the phosphorus of liquid manure, there are several viable methods for reducing its content or its total separation. The phosphorus content can be effectively reduced simply by separating solids and liquid from each other, for example through mechanical separation, whereby a considerable portion of phosphorus remains with the solid fraction. On the other hand, phosphorus can be effectively precipitated from liquid manure chemically, either for ammonium magnesium phosphate (struvite), in which case the nutrients included in the precipitate are in a form useful for plants, or by a method generally used in sewage treatment facilities by precipitating with a trivalent iron or aluminum salt ($Fe^{3+}$, $Al^{3+}$). Nitrogen is considerably more challenging than phosphorus in terms of concentrating or separating. In mechanical separation, most of the nitrogen remains in the liquid fraction. In practice, bonding chemically by using a reagent is difficult and just some of the nitrogen can be separated. Separation of the liquid manure ammonia on a countercurrent tower principle (ammonia stripping) has not been implementable thus far in an economically viable manner.

Nitrogen in Liquid Manure

Liquid manure contains nitrogen both in an organic and inorganic form in high concentrations. The average content of soluble nitrogen in liquid swine manure is 2.5 kg/ton, the average total nitrogen content being 3.8 kg/ton. Liquid bovine manure has a total nitrogen content of 3.0 kg/ton, the content of soluble nitrogen being 1.8 kg/ton (Soil Analysis Service statistics). The difference between total nitrogen and soluble nitrogen represents the amount of organic nitrogen contained in liquid manure. Most of the nitrogen has its source in urine and hydrolyzes enzymatically into ammonium within just a few first days from the beginning of storage. For the most part, the soluble nitrogen contained in liquid manure consists of ammonium. With respect to waste water, the nitrogen content of liquid manure is approximately tenfold.

Methods Used for Separating Liquid Manure Nitrogen

The separation of liquid manure nitrogen has resulted in developing and testing a multitude of various methods. These include, among others, various chemical precipitation methods, ion exchange, various membrane filtration methods, biological separation methods, as well as separation of ammonia on a countercurrent tower principle (ammonia stripping). What is typical for most of the methods is the inadequacy to achieve an acceptable standard regarding the separation of ammonia and the economically fairly high price.

Separation of Solids and Liquid

Physical separation has been found to have but a slight effect on a nitrogen fraction dissolved in liquid.

Settling and Mechanical Separation

In mechanical separation, most of the nitrogen remains within the liquid fraction.

Biological Methods

Regarding biological methods, the method that is best known and in common use, particularly as an effluent nitrogen separation method, is a nitrification/denitrification process. Nitrification-denitrification is a two-stage oxidation-reduction process. There, nitrogen is first allowed to oxidize into a nitrate form, i.e. to nitrify. Then, there is needed an oxygen-free denitrification stage, in which the nitrate nitrogen reduces into a nitrogen gas. The method requires precise optimum conditions in order to work.

Other biological nitrogen separation methods have also been developed. As for these, the anaerobic ammonium oxidation reaction (anammox), still under development, has perhaps drawn most attention. The method comprises the oxidation of ammonium directly into a nitrogen gas ($N_2$) while NO2 functions as an electron acceptor. The method is only in an ongoing development stage.

A problem with all biological nitrogen separation methods are fairly high investment and maintenance costs. In the methods, nitrogen is not reclaimed but released as a gas in the atmosphere.

Filtration

Although filtration has been used mainly for the retention of solids, the chemical and possibly also biological properties of a filtered solution are also influenced by filtration. However, the reductions of nitrogen compounds present in a form dissolved in liquid have not been higher than 10%, even at their best.

Reverse Osmosis

Reverse osmosis is a pressure-based membrane purification technique. The principle is based on the use of pressure for forcing a solvent (usually pure water) to pass through a semipermeable membrane from a solution of higher concentration towards one of lower concentration, i.e. the opposite way with respect to osmosis. Making the method applicable to liquid manure nitrogen separation requires a pretreatment of liquid manure (sedimentation, precipitation, microfiltration).

Electrochemical Methods

Electroflotation is a separation method, wherein light particles rise to the surface of wastewater along with small gas bubbles. In this method, the surfaces of electrodes (anode and cathode) develop by way of electrolysis of water small hydrogen and oxygen gas bubbles (22-50 micrometers in diameter). The bubbles rise to the surface of liquid and function at the same time as collectors of finely divided small particles. Electrolysis calls for a powerful electric current. The process is limited by the high dry matter content of liquid manure. In order to enable also for an effective removal of soluble nitrogen, the method requires simultaneous electrochemical oxidation.

Electrochemical Oxidation

There are a variety of ways to carry out electrochemical oxidation. A well-known/common method is the use of chlorine and at-anode formed hypochlorite for the oxidation of ammonia. In the method, the decomposition of ammonium occurs by way of an indirect oxidation reaction. The decomposition takes place through the intermediary of powerful oxidants generated in a liquid solution in an electrochemical reaction. In the presence of chloride, there is chlorine gas generated at the anode. The anode reaction is followed by a diffusion of chlorine gas in the liquid solution (dissolution) and further by a protolyzation into hypochlorite and hypochlorous acid, depending on pH. The method has its effectiveness depending on a salt to be added and the strength of electric current. The effective oxidation of ammonia requires typically a chloride dose of 30 g/L. The problem is a possible formation of chlorinated organic intermediates.

Nitrogen Separation by Stripping

The method comprises reducing the content of ammonia in a liquid phase by passing it in a tower into a gas phase. The method is based on raising first the pH of liquid manure for converting the ammonium nitrogen contained therein into ammonia. This is followed by driving the liquid manure through a tower filled with a packing material promoting the evaporation of $NH_3$, such that the liquid manure is fed into the tower by way of its top end while blowing air into the tower from its bottom part, this resulting in the desorption of ammonia, i.e. its passage into a gas phase from the (boundary) surface of slurry trickling downwards in the packing material. The ammonia gas separated into a gas phase is further passed into water or acid, in which the ammonia gas adsorbs into liquid.

The evaporation of ammonium depends on pH and temperature of the solution. With a rising pH, the ammonium ion dissociates and forms hydrogen ions and ammonia. The resulting hydrogen ions bond with negative OH ions to produce water. $[NH_4^+ + OH^- \rightleftharpoons NH_3 + H_2O]$. This equilibrium depends on pH and temperature. In a neutral solution (pH 7), the amount of ammonia molecules in proportion to the total amount of ammonium ions and ammonia molecules is only 0.39%, while that proportion at pH 9 is 28.4% at the temperature of 20 degrees.

Ammonia is very volatile, but also highly soluble in water. According to Henry's law, at a constant temperature, the amount of a given gas dissolved in a given type and volume of liquid is directly proportional to the partial pressure of that gas in equilibrium with that liquid. Thus, it is a consequence of the Henry's law that the partial pressure of ammonia gas on the surface of a slurry solution is directly proportional to the molar ratio of ammonia in the slurry.

Stripping is carried out by using a tower or a tower which is packed with a material with a capability of attaining a specific surface area as large as possible while generating an air resistance as low as possible. As a result, the desorption, i.e. the passage of ammonia from a boundary surface into a gas phase, is achieved effectively. In the tower, air and water are flowing in countercurrent relative to each other, whereby, as the water is flowing down along the surface of a packing material in the form of a film, the air flows upward in the form of a continuous phase. The air flow must be sufficiently powerful and turbulent in order to prevent the air in the proximity of the packing material surface from becoming concentrated with ammonia gas and to provide an effective removal of ammonia. A turbulence of the liquid flow would also be welcome.

A stripping tower has been tested for the separation of liquid manure nitrogen, but this has involved problems because of which the method has not gained the status of general practice, with the exception of research experiments. The reasons can be broken down as follows:

1) The high dry matter content of liquid manure causes clogging of the tower and hampers the progress of stripping; 2) Stripping requires a sufficiently high pH value for the solution to enable a separation of ammonium in the tower as ammonia gas. The untreated liquid manure has a PH of about 7.4. At this pH, the amount of ammonia molecules is only about 1% in proportion to the total amount of ammonium ions and ammonia molecules, while the respective proportion at the pH of 8.8 is already up to about 20%. Changing the pH of liquid manure is difficult because of a high buffer capacity contained in liquid manure. Raising the pH of raw liquid manure requires the use of a large amount of chemicals, making the process economically non-viable; 3) The removal of nitrogen involves a powerful odor problem as untreated liquid manure is passed into the tower and the odor travels along with the air flow; 4) In industry, stripping is generally effected by using a single tall tower (at least 7 m in height, USEPA 2000). A condition in this type of technology is that the supplied solution has its nitrogen as far as possible in the form of ammonia. With the separation of ammonia, the solution's pH decreases and the tower's capacity to separate nitrogen is falling. In industry, the solutions are often 100% ammonia. The implementation of a single tall tower incurs extra costs because of technical solutions called for by the tower's height, resulting in a technical design which is fairly expensive.

SUMMARY OF THE DISCLOSURE

It is an objective of the present invention to provide a method for treating and/or pre-treating liquid manure or biogas plant reject for the elimination of harmful substances, particularly nitrogen, phosphorus, and odor molecules, said method comprising the use of an apparatus which includes at least two functionally sequential treatment tanks for conducting a biological treatment on a matter to be treated, said tanks comprising inlet means for supplying the tank with a substance to be treated, outlet means for passing the post-treatment matter out of the tank, and air inlet means for supplying the tank with air required by a biological process, said method being characterized in that each process tank is first provided with a microbe population adapted for processing the matter to be treated; the matter to be treated is supplied gradually into the first process tank and thence further into a subsequent process tank/subsequent process tanks, such that the microbe population first provided in the process tanks displaces step by step the original microbe population present in the matter to be treated; that the matter substantially free of original microbes and present in a final process tank is returned into the first process tank for diluting the matter to be treated and fed into the first process tank; and that the method comprises conducting downstream of at least one process tank a nitrogen removal treatment by supplying a stripping tower with the matter to be treated from the process tank, in which the pH of the matter to be treated has been raised by means of a microbiological treatment to a level sufficient from the standpoint of nitrogen removal without a chemical addition.

The developed microbiological treatment system for liquid manure is based on i) adding liquid manure in an appropriate amount to an existing microbial growth/colony instead of adding a microbial preparation in a small amount (microbe 'inoculation') to liquid manure. The principle is that the existing microbe colony of liquid manure is possible to displace, provided that it has an underrepresented presence in a dominating microbe community with abundant diversity of species in conditions which favor the dominating microbe community. ii) Having developed around the deodorization of liquid manure a technical system to support the activity of a microbe colony in the deodorization process. The system enables a) creating and maintaining optimum conditions for the developed microbe community, b) and conditions allowing for a further development of the community. In the initial stage of processing, the system is filled with the developed microbial growth.

The developed microbe community is isolated from soil and adapted to the treatment of liquid manure. The soil, from which the isolation has been conducted, has been in farming for decades and has been fertilized with liquid manure. The soil has also a highly abundant presence of earthworms. In the isolation process, the soil has been worked into a soil-water suspension, having liquid manure added therein little by little. The community has been upgraded in laboratory conditions for several years to make it good for the deodorization treatment of liquid manure. The community does not include genetically engineered organisms, but it has developed by way of mutations, natural selection, and genetic combinations that have taken place spontaneously by nature. Microbial strains capable of breaking up odor compounds have been identified and are known in abundance (e.g. Rappert and Muller, 2005, U.S. Pat. No. 5,811,287).

BRIEF DESCRIPTION OF THE DRAWINGS

The invention will now be described more closely with reference to the accompanying drawing, which shows in FIG. 1 a diagrammatic view of one apparatus useful for carrying out the method.

DETAILED DESCRIPTION OF THE DISCLOSURE

The apparatus shown in FIG. 1 comprises process tanks 5, which are intended for a microbiological treatment and which are initially filled with a microbial population isolated from soil. In the illustrated embodiment there are six examples of process tanks and those are interconnected in such a way that the matter to be treated, such as e.g. liquid manure or biogas plant reject, is able to flow from one tank to the next. Each process tank 5 is provided with air inlet means in communication with a source of compressed air 2. The matter to be treated is first supplied by means of a feed pump 1 into a collecting tank 3, in which a separation of coarse matter is conducted. From the collecting tank 3, the matter to be treated is delivered by means of a feed pump 4 into a first treatment tank 5 and thence further to subsequent tanks, such that the microbial population provided initially in the tanks displaces in a step-by-step manner the original microbial population present in the matter to be treated. From a stripping tower 22A is provided a feedback by means of a feed pump 8 to the first treatment tank 5 for returning the matter substantially free of original microbes into the first treatment tank 5 for diluting the matter to be treated and fed therein. The feedback takes place preferably at a ratio 1:1 for enhancing the process. In the first treatment tank 5 occurs the breakdown of toxic compounds with enzymes, which are first to function. The displacement of a microbial population present in liquid manure does not begin to proceed more effectively until in a second treatment tank. During an aerobic biological process, the pH of liquid manure rises from a pH value 7.5 preferably to a value not lower than 8.5, typically to a value 8.8-9.0. This is a sufficiently high pH to enable conveying the matter to be treated into the stripping tower 22A, which is positioned downstream of a final treatment tank and in which about ⅓ of the nitrogen content can be separated without a chemical addition.

In the embodiment of FIG. 1, the matter to be treated is conveyed, downstream of the first stripping tower 22A, by a feed pump 9 into a treatment tank 10, in which is effected the addition of magnesium oxide (MgO) from a magnesium oxide tank 12 by means of a chemical pump 11. Reference numeral 13 represents a blender. From the treatment tank 10, the matter to be treated is conveyed by a feed pump 14 into a second stripping tower 22, wherein the slurry is collected in an equalizing tank 25 and conducted further through a heater 26 by a feed pump 20 into a third stripping tower 22. Upstream of the third stripping tower 22, the slurry type matter to be treated is supplemented, for raising the pH, with lime ($Ca(OH)_2$) or sodium hydroxide (NaOH) from a tank 18 by means of a feed pump 16. After this supplement, the matter to be treated is conveyed into the third stripping tower 22. The number of sequential stripping towers may even be more than that. Air supply to nitrogen removal (into the stripping towers) is effected by a fan 21. The air supplied to nitrogen removal is warmed up by a heater 27. From the stripping tower, the air is passed for washing into a water or sulphuric acid tank 24 for collecting nitrogen. The liquid manure is conveyed from the final stripping tower 22 by way of a pipe 28 to further fractionation, for example through precipitation tanks, and the purified water is removed from a final precipitation tank.

Reference numeral 25 is used to represent equalizing vessels for the slurry flow, and reference numeral 26 represents heating of the slurry before each of the stripping towers 22A and 22. Reference numeral 28 is used to represent a pipe, by way of which the now non-odorous treated slurry, having nitrogen removed therefrom, is conveyed to further fractionation e.g. by means of chemicals in the precipitation tanks The chemicals may comprise e.g. ferric sulphate (Fe2(SO4)3, aluminum sulphate ($Al_2(SO_4)_3$), and calcium carbonate ($CaCO_3$). From the precipitation tank, the precipitate is conveyed by a precipitate transfer pump into a precipitate drying silo, from which the compressed liquids are passed to the beginning of the process into the collecting tank 3.

During an aerobic biological process, the pH of liquid manure rises. As ammonia is released, the solution's pH falls, whereby the equilibrium between bicarbonate and carbon dioxide changes in favor of carbon dioxide, some carbon dioxide also releasing from the solution as a gas in the atmosphere. Removing/releasing ammonium and carbonate from liquid manure enables a considerable reduction in the buffer effect of liquid manure.

In liquid manure, the change of pH is subjected to a complex buffer system, consisting of ammonium, carbonates, volatile fatty acids, and other organic compounds. Most of the nitrogen of liquid manure comes in urea contained in urine. One of the most essential impeding factors regarding the separation of nitrogen has to do with the high buffer capacity of liquid manure.

Theory Regarding the Buffer Reaction of an Ammonium Carbonate System

The enzymatic hydrolysis of urea obtained from urine into ammonium carbonate:

$$CO(NH_2)_2 \xrightarrow{Urease, H2O} 2NH_4^+ + CO_3^{2-} \quad (1)$$

the further decomposition of ammonium carbonate into ammonia:

$$2NH_4^+ + CO_3^{2-} \rightleftharpoons NH_4^+ + HCO_3^- + NH_3 \quad (2)$$

and into carbon dioxide:

$$NH_4^+ + HCO_3^- \rightleftharpoons CO_2 + H_2O + NH_3. \quad (3)$$

If the released gases escape in the atmosphere, the equations (2) and (3) proceed to the right. The equations demonstrate how, on the one hand, protons are released in hydrolysis and, on the other hand, protons are bound by the release of carbon dioxide.

Hydrolysis of ammonium:

$$NH_4^+ \rightleftharpoons NH_3 + H^+ \quad (4)$$

Release of carbon dioxide:

$$CO_3^{2-} + H^+ \rightleftharpoons HCO_3^- \quad (5)$$

$$HCO_3^- + H^+ \rightleftharpoons CO_2 + H_2O. \quad (6)$$

Hydrolysis of ammonium equilibrium constant pKa $NH_4$=9.3, evaporation of ammonia only occurs in neutral or alkaline conditions. Protons are released in the evaporation of ammonia.

During a microbiological aerobic process, the amount of fatty acids present in liquid manure decreases as a result of microbiological decomposition activity. It can be seen from the equation below that the reaction consumes protons.

$$CH_3COO^- + H^+ \rightleftharpoons CH3COOH$$

$$CH3COO^- + H^+ + 2O_2 \rightleftharpoons 2CO_2 + 2H_2O$$

After liquid manure has been driven through a stripping tower, its pH can be changed with a significantly smaller amount of chemicals than before the removal of ammonium and carbonate from liquid manure, or liquid manure can have its pH re-raised by using an aerobic biological process. In this case, the separation of ammonia by stripping can be conducted in stages by using several shorter towers in place of a commonly employed single tall tower (see USEPA 2000). The separation of ammonia in series and/or parallel interconnected towers is more efficient than stripping conducted in a single tall tower. Ammonium-depleted liquid manure can still be used in the process for feedback. Ammonia is toxic for organisms and cells. In cell growths, ammonia has been found contributing to cellular apoptosis (programmed cell death). Although the toxicity mechanisms of ammonia have not become thoroughly understood, it is known to interfere with the electrochemical gradient of a cell. A high concentration of ammonia in the growth environment induces cytoplasmic acidification. Thus, in order to maintain pH homeostasis, the energy consumption of cells increases. In enzymatic processes, the accumulation of product may begin to inhibit reaction (end product inhibition). Making the feedback with liquid manure, the ammonium content of which has been lowered, enables reducing the toxicity and product inhibition of ammonia and thereby enhancing the biological process. The ability to enhance the process results in a shorter process residence time, whereby the size of reactors can be reduced. During a biological aerobic process, the liquid manure becomes odorless and more fluid. Thus, the liquid manure is easy to supply in and expel from the tower, nor does the air blasted through the tower cause odor problems in the vicinity. The matter to be treated is preferably adapted to circulate in at least one stripping tower for several times, prior to its transfer to the next process step.

In the above-described embodiment, the stripping towers are shown as disposed downstream of the final process tank, but it is preferred that one or more stripping towers be positioned functionally between two successive process tanks The stripping towers without a chemical addition operate essentially also as process tanks, providing a possibility of reducing the number of process tanks from the exemplified six tanks to e.g. three tanks for reaching the same total nitrogen removal. Preferably, the number of stripping towers 22A is not less than three prior to raising pH to a value >9 by a chemical addition. The number of stripping towers without a chemical addition can also be one or more downstream of the last actual process tank. After the chemical addition, pH rises to a value >9, at which time the biological process stops working with the death of the microbe population.

The invention claimed is:

1. A method for treating and/or pre-treating liquid manure or biogas plant reject for the elimination of harmful substances, particularly nitrogen, phosphorus, and odor molecules, said method comprising the use of an apparatus which includes at least two functionally sequential process tanks for conducting a biological treatment on a matter to be treated, said process tanks comprising inlet means for supplying the process tank with a substance to be treated, outlet means for passing the post-treatment matter out of the tank, and air inlet means for supplying the process tank with air required by an aerobic biological process, wherein the method comprises:

providing each process tank first with a microbe population adapted for processing the matter to be treated;

supplying the matter to be treated gradually into the first process tank and thence further into a subsequent process tank/subsequent process tanks, such that the microbe population first provided in the process tanks displaces step by step the original microbe population present in the matter to be treated;

returning the matter substantially free of original microbes and present in a final process tank into the first process tank for diluting the matter to be treated and fed into the first process tank;

providing air required for an aerobic microbiological treatment to at least one process tank through the air inlet means thereof so as to raise the pH of the matter in the at least one process tank to a level of not lower than pH 8.5 and remove a portion of the nitrogen therefrom, to produce an aerobic microbiological treated matter; and conducting a nitrogen removal treatment in a stripping tower by supplying the stripping tower with the aerobic microbiological treated matter from the at least one process tank.

2. A method as set forth in claim 1, characterized in that the matter to be treated is fed from the process tank into the first stripping tower without a chemical addition.

3. A method as set forth in claim 1, wherein the matter present in the stripping tower is circulated internally several times.

4. A method as set forth in claim 1, wherein the method comprises raising pH in a process tank upstream of the stripping tower by means of a biological treatment to a value of about pH 8.8-9.0.

5. A method as set forth in claim 1, wherein the number of stripping towers operating without a chemical addition is at least 3 prior to raising pH to a value >9 by a chemical addition.

6. A method as set forth in claim 1, wherein the method comprises using at least one additional stripping tower in which is conducted a chemical addition for raising the pH of a matter to be treated and fed therein to a pH value necessitated by the process.

7. A method as set forth in claim 1, wherein the matter to be returned into the first process tank is drawn in downstream of the stripping tower operating without a chemical addition.

8. A method as set forth in claim 6, wherein the pH-raising chemical is provided by using magnesium oxide (MgO) or calcium hydroxide $Ca(OH)_2$, whereby the pH is raised to a value of about 9.5-10.

9. A method as set forth in claim 1, wherein the at least one stripping tower, operating without a chemical addition, is positioned functionally at a location between two tanks.

* * * * *

UNITED STATES PATENT AND TRADEMARK OFFICE
CERTIFICATE OF CORRECTION

PATENT NO. : 9,527,759 B2
APPLICATION NO. : 12/937604
DATED : December 27, 2016
INVENTOR(S) : Alitalo et al.

It is certified that error appears in the above-identified patent and that said Letters Patent is hereby corrected as shown below:

On the Title Page

Assignee reads:
Pellon Group Oy, Yilhärmä (FI)

Should read:
Pellon Group Oy, Ylihärmä (FI)

In the Claims

At Column 8, Claim 1, the text "A method for treating and/or pre-treating liquid manure or biogas plant reject for the elimination of harmful substances, particularly nitrogen, phosphorus, and odor molecules, said method comprising the use of an apparatus which includes at least two functionally sequential process tanks for conducting a biological treatment on a matter to be treated, said process tanks comprising inlet means for supplying the process tank with a substance to be treated, outlet means for passing the post-treatment matter out of the tank, and air inlet means for supplying the process tank with air required by an aerobic biological process, wherein the method comprises:
    providing each process tank first with a microbe population adapted for processing the matter to be treated;
    supplying the matter to be treated gradually into the first process tank and thence further into a subsequent process tank/subsequent process tanks, such that the microbe population first provided in the process tanks displaces step by step the original microbe population present in the matter to be treated;
    returning the matter substantially free of original microbes and present in a final process tank into the first process tank for diluting the matter to be treated and fed into the first process tank;
    providing air required for an aerobic microbiological treatment to at least one process tank through the air inlet means thereof so as to raise the pH of the matter in the at least Signed and Sealed this
Eleventh Day of April, 2017

Michelle K. Lee
*Director of the United States Patent and Trademark Office*

CERTIFICATE OF CORRECTION (continued)
U.S. Pat. No. 9,527,759 B2 one process tank to a level of not lower than pH 8.5 and remove a portion of the nitrogen therefrom, to produce an aerobic microbiological treated matter; and
conducting a nitrogen removal treatment in a stripping tower by supplying the stripping tower with the aerobic microbiological treated matter from the at least one process tank."

Should be changed to:
-- A method for treating and/or pre-treating liquid manure or biogas plant reject for the elimination of harmful substances, particularly nitrogen, phosphorus, and odor molecules, said method comprising the use of an apparatus which includes at least two functionally sequential process tanks for conducting a biological treatment on a matter to be treated, said process tanks comprising inlet means for supplying the process tank with a substance to be treated, outlet means for passing the post-treatment matter out of the tank, and air inlet means for supplying the process tank with air required by an aerobic biological process, wherein the method comprises:
isolating a microbe population from soil, wherein isolating the microbe population includes working the soil into a soil-water suspension and incrementally adding the matter to be treated into the soil-water suspension for a period of time to produce an adapted microbe population for a deodorization treatment of the matter to be treated;
providing each process tank first with the adapted microbe population for processing the matter to be treated;
supplying the matter to be treated gradually into a first process tank and thence further into a subsequent process tank/subsequent process tanks, such that the adapted microbe population first provided in the process tanks displaces step by step an original microbe population present in the matter to be treated;
supplying compressed air to the matter to be treated in the process tanks for an aerobic microbiological treatment through the air inlet means of the at least one process tank so as to raise the pH of the matter in the at least one process tank to a level of not lower than pH 8.5 and remove a portion of the nitrogen therefrom, to produce an aerobic microbiological treated matter;
returning the matter substantially free of original microbes and present in a final process tank into the first process tank for diluting the matter to be treated and fed into the first process tank; and
conducting a nitrogen removal treatment in a stripping tower by supplying the stripping tower with the aerobic microbiological treated matter from the at least one process tank; and
returning the matter substantially free of original microbes from the stripping tower into the first process tank for diluting the matter to be treated and fed into the first process tank. --